(12) United States Patent
Squicciarini

(10) Patent No.: US 7,503,892 B2
(45) Date of Patent: Mar. 17, 2009

(54) MALE PROSTHESIS DEVICE

(76) Inventor: John B. Squicciarini, 13 Wisteria Pl., Aliso Viejo, CA (US) 92656

( * ) Notice: Subject to any disclaimer, the term of this patent is extended or adjusted under 35 U.S.C. 154(b) by 16 days.

(21) Appl. No.: 11/733,347

(22) Filed: Apr. 10, 2007

(65) Prior Publication Data

US 2007/0238918 A1 Oct. 11, 2007

Related U.S. Application Data

(60) Provisional application No. 60/791,149, filed on Apr. 10, 2006.

(51) Int. Cl.
*A61B 5/00* (2006.01)
(52) U.S. Cl. ...................................... 600/39
(58) Field of Classification Search ............ 600/38–41; 128/842, 844, 845; 623/24, 25, 57
See application file for complete search history.

(56) References Cited

U.S. PATENT DOCUMENTS

| | | | |
|---|---|---|---|
| 4,671,262 A | 6/1987 | West | |
| 4,690,135 A | 9/1987 | Gerow | |
| 5,076,287 A | 12/1991 | Johnson | |
| 5,137,032 A | 8/1992 | Harmon | |
| 5,201,327 A | 4/1993 | Johnson | |
| 5,413,611 A * | 5/1995 | Haslam et al. | 623/25 |
| 5,823,939 A | 10/1998 | Tsagarakis | |
| 5,984,880 A * | 11/1999 | Lander et al. | 600/595 |
| 6,246,915 B1 | 6/2001 | Boutos | |
| 6,266,560 B1 | 7/2001 | Zhang et al. | |
| 6,350,230 B1 | 2/2002 | Kontos | |
| 6,547,717 B1 | 4/2003 | Green et al. | |
| 6,599,236 B1 | 7/2003 | Castro | |
| 6,695,770 B1 | 2/2004 | Choy et al. | |
| 6,749,558 B1 | 6/2004 | Brintle | |
| 6,814,695 B1 | 11/2004 | Wyllie et al. | |
| 7,104,950 B2 * | 9/2006 | Levy | 600/38 |
| 7,186,212 B1 | 3/2007 | McMullen | |
| 2003/0036678 A1 * | 2/2003 | Abbassi | 600/38 |
| 2004/0082831 A1 * | 4/2004 | Kobashikawa et al. | 600/38 |
| 2006/0189949 A1 | 8/2006 | Tomosada et al. | |
| 2006/0270897 A1 * | 11/2006 | Homer | 600/38 |

* cited by examiner

*Primary Examiner*—Samuel G Gilbert
(74) *Attorney, Agent, or Firm*—Knobbe, Martens Olson & Bear, LLP

(57) ABSTRACT

A male prosthesis device configured to be worn on a flaccid, partially-erect or erect penis which transmits tactile sensations through a stimulation material to the surface of the penis. The device includes a prosthesis with an outer surface and in inner chamber, a microprocessor, one or more sensors and one or more stimulation materials. The outer surface is configured to appear as a penis or other elongate body with hard or soft materials, with optional stimulation materials and sensors. The inner cavity is lined with stimulation material configured to contact the surface of the penis. Sensors for detecting sensation or direction can be disposed within, on, or separate from the device transmit signals electrically or wirelessly to the microprocessor, which is programmed to generate stimulation sensations in response to signals from the sensors, stimulation materials, or controllers that are transmitted to the stimulation material.

9 Claims, 1 Drawing Sheet

MALE PROSTHESIS DEVICE

CROSS-REFERENCE TO RELATED APPLICATIONS

This application claims the benefit of priority from U.S. Provisional No. 60/791,149, filed Apr. 10, 2006, which is incorporated by reference in its entirety herein.

BACKGROUND OF THE INVENTION

1. Field of the Invention

The invention relates generally to the field of improving sexual relationships, stimulation and sensation, and more specifically to a male prosthesis device to be worn over a penis. The male prosthesis device uses sensors and tactile stimulators to convey sensations to the surface of the penis. The invention enables men suffering from erectile dysfunction to feel a sensation of sexual intercourse or other stimulation on a flaccid, partially-erect, or erect penis. The device can be used to improve sexual satisfaction and for therapeutic reasons in treating erectile dysfunction and other sexual or genitalia related conditions for both men and women.

2. Description of the Related Art

Many men have erectile dysfunction problems which renders them unable to perform sexually. The problems can be physical, emotional, or psychological, or a combination of such factors. Some solutions include drugs or other chemical or hormonal aid. However, the side effects of drugs are seldom completely understood, and may over the long term exacerbate the problem or lead to other problems. Other solutions include surgery to the sexual organs. Surgery is often inaccurate or risky, and may not address the real problem. What is needed is a male prosthesis device that enables a man to experience the actual sensations of a sexual event, while avoiding invasive and/or detrimental effects or drugs or surgery.

SUMMARY OF THE INVENTION

Accordingly, there is a need for apparatus, systems, and methods that safely and reliably produce sensations of a sexual event for a man irrespective of the condition of his penis. This document discloses a system and method to simulate sexual copulation sensitivity, primarily for men who are unable to perform sexually for any reason. In one aspect, a system includes a male prosthesis device. The device includes a specially-designed, electronically-controlled stimulation prosthesis configured to fit over a flaccid or partially-erect penis. The prosthesis allows both partners in a sexual activity to feel the sensations of an actual sexual experience. The sensations are generated through the controlled release of electrical energy, which are controlled by a microprocessor and managed by one or more sensitivity and direction detection sensors included with the prosthesis device.

The details of one or more embodiments are set forth in the accompanying drawings and the description below. Other features and advantages will be apparent from the description and drawings, and from the claims.

In one embodiment of the present invention, a male prosthesis device includes a prosthesis, a sensor, a microprocessor and stimulation material. The prosthesis has an outer surface and an inner cavity, where the inner cavity is sized and adapted to receive a penis. The sensor is integrated with the prosthesis for sensing a movement, pressure and/or force of the prosthesis in an activity. The sensor is configured to generate signals based upon such movement, pressure and/or force. The microprocessor receives signals from the sensor and is adapted to generate a signal intended to represent a sensation. The stimulation material covers at least a portion of the surface of the inner cavity for receiving the signal representing a sensation.

In another embodiment of the present invention, a male prosthesis device includes a prosthesis, a sensor, a microprocessor, a first stimulation material and a second stimulation material. The prosthesis has an outer surface and an inner cavity, where the inner cavity is sized and adapted to receive a penis. The sensor is integrated with the prosthesis for sensing a movement, pressure and/or force of the prosthesis in an activity. The sensor is configured to generate signals based upon such movement, pressure and/or force. The microprocessor receives signals from the sensor and is adapted to generate a signal intended to represent a sensation. The first stimulation material covers at least a portion of the surface of the inner cavity for receiving the signal representing a sensation. The second stimulation material covers at least portion of the outer surface of the prosthesis and is configured to receive the signal representing a sensation.

BRIEF DESCRIPTION OF THE DRAWINGS

These and other aspects will now be described in detail with reference to the following drawings.

Figure 1:
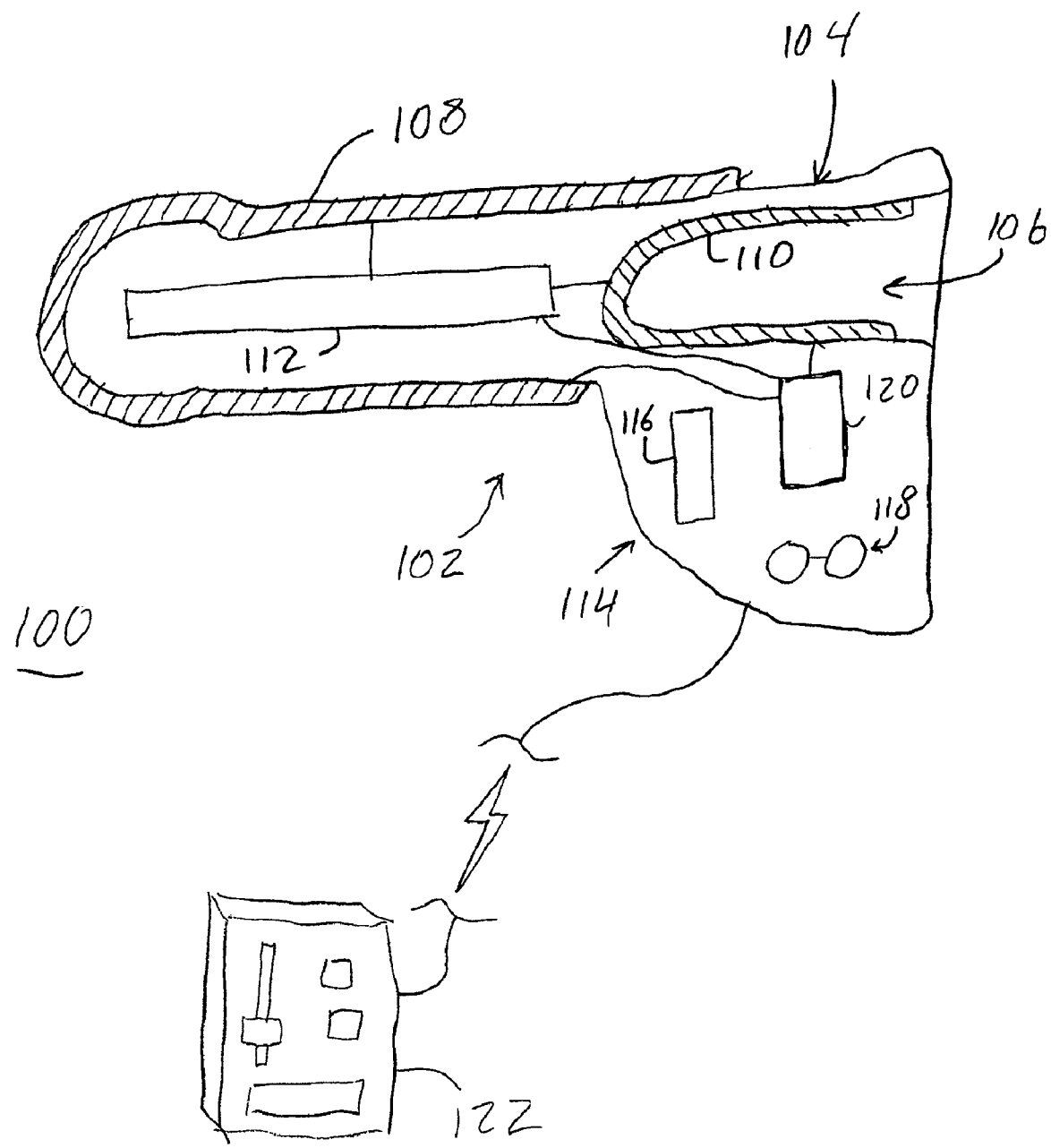
FIG. 1 is a schematic cross-section view of one embodiment of a male prosthesis device.

Like reference symbols in the various drawings indicate like elements. Throughout the figure(s), the same reference numerals and characters, unless otherwise stated, are used to denote like features, elements, components or portions of the illustrated embodiments. Moreover, while the subject invention will now be described in detail with reference to the figure(s), it is done so in connection with the illustrative embodiments. It is intended that changes and modifications can be made to the described embodiments without departing from the true scope and spirit of the subject invention as defined by the appended claims.

DETAILED DESCRIPTION OF THE PREFERRED EMBODIMENT

This documents describes a male prosthesis device, as well as systems and methods employing a male prosthesis device, for providing electronically simulated sensations and stimuli of a sexual experience, primarily for men who have erectile dysfunction problems.

FIG. 1 shows a male prosthesis device 100 in accordance with preferred embodiments. The male prosthesis device 100 includes a prosthesis 102 configured and shaped to resemble the look and feel of an erect penis. The prosthesis 102 includes an outer surface 104 and an inner cavity 106 sized and shaped to allow a flaccid or partially erect penis to be inserted therein. The prosthesis 102 can be made of any semi-rigid yet soft material such as rubber, silicone, or the like.

The male prosthesis device 100 further includes external stimulation material 108 that covers at least a portion of the outer surface 104, and an internal stimulation material 110 that covers at least a portion of the inner cavity 106. In some preferred embodiments, the external stimulation material 108 covers a major portion of the outer surface 104, and the internal stimulation material 110 covers a major portion of the inner cavity 106. The external and internal stimulation material 108, 110 are electronically controlled, and configured to receive and/or deliver electronically controlled stimuli based on electric signals generated from a sensitivity and/or direction sensor 112. The sensor 112 can be mounted on the other surface 104, or contained within the prosthesis 102, or be configured to be both mounted on and contained within the prosthesis 102. The sensor 112 can be electrically or physically connected with the external stimulation material 108 and/or internal stimulation material 110.

A bag 114 of the male prosthesis device 100 includes batteries 116, controllers 118 and a microprocessor 120. The microprocessor 120 can be embodied in two or more processors. The sensor 112 provides input to the microprocessor 120 as to the movement (directionally, degree of force or sensitivity, etc.) and pressure experienced by the prosthesis 102 for approximating sexual sensations. The microprocessor 120 then generates an electronic representation of the sensation and delivers the electronic representation to the internal stimulation material 110, for providing sexual sensations to the penis, and/or to the external stimulation material 108 for providing sexual sensations to a vagina or other cavity.

The controllers 118 control and modulate the microprocessor 120 so as to adjust the level and intensity of the electronic representation of the sensation. An optional external controller 122 provides independent control of the electronic stimulation level to the penis and/or cavity, and onto the prosthesis 102 to give users full control over the intensity of the stimulation and sensations. The external controller 122 can communicate to the microprocessor 120 via a wired or wireless communication channel.

In operation, as the male prosthesis device 100 is inserted into a cavity such as a vagina, the penis inside the inner cavity 106 receives electronically generated sensory signals, preferably directed to the tip of the penis head, via a portion of the internal stimulation material 108. As the male prosthesis device 100 is inserted further into the cavity, the electronically generated sensory signals are delivered further along the penis shaft by the internal stimulation material 108.

Although a few embodiments have been described in detail above, other modifications are possible. Other embodiments may be within the scope of the following claims. It will be understood that the foregoing is only illustrative of the principles of the invention, and that various modifications, alterations, and combinations can be made by those skilled in the art without departing from the scope and spirit of the invention. Accordingly, it is not intended that the invention be limited, except as by the appended claims.

What is claimed is:

1. A therapeutic male prosthesis device for simulating natural sensations, the device comprising:
   a unitary prosthetic body comprising an outer surface and an inner cavity integral with the unitary body, the inner cavity sized and adapted to receive a penis, the outer surface configured and shaped to resemble the look and feel of an erect penis; and
   a simulation unit comprising a sensor, a microprocessor, and stimulation material, at least a part of the simulation unit positioned between and proximal to the unitary body outer surface and the unitary body inner cavity, the sensor integrated with the prosthesis for sensing a movement, pressure and/or force of the prosthesis in an activity approximating sexual sensations; the sensor configured to generate signals based upon such movement, pressure and/or force in an activity approximating sexual sensations, the microprocessor configured for receiving signals from the sensor, the microprocessor adapted to generate a signal intended to represent a sensation in an activity approximating sexual sensations; and the stimulation material covering at least a portion of the surface of the inner cavity for receiving the signal representing a sensation on a penis.

2. A male prosthesis device in accordance with claim 1, further comprising stimulation material covering at least portion of the outer surface of the unitary body, and configured to receive the signal representing a sensation for providing sexual sensations to a cavity.

3. A male prosthesis device in accordance with claim 1, further comprising a bag.

4. A male prosthesis device in accordance with claim 1, further comprising a battery.

5. A male prosthesis device in accordance with claim 1, further comprising a controller configured to control intensity of the sensation.

6. A male prosthesis device in accordance with claim 5, further comprising a communication channel between the controller and the microprocessor.

7. A male prosthesis device in accordance with claim 6, wherein the communication channel between the controller and the microprocessor is wireless.

8. A male prosthesis device in accordance with claim 1, wherein the unitary prosthetic body is configured to sense an insertion sensation of the unitary prosthetic body in a cavity and generate a sensation further along the inner cavity with the stimulation material simulating the insertion sensation.

9. A method of simulating sexual sensations between a penis and a cavity, comprising:
   inserting a penis in a unitary prosthetic body comprising an outer surface and an inner cavity integral with the unitary body, the inner cavity sized and adapted to receive a penis, the outer surface configured and shaped to resemble the look and feel of an erect penis; the unitary prosthetic body further comprising a simulation unit comprising a sensor, a microprocessor, and stimulation material, at least a part of the simulation unit positioned between and proximal to the unitary body outer surface and the unitary body inner cavity, the sensor integrated with the prosthesis for sensing a movement, pressure and/or force of the prosthesis in an activity approximating sexual sensations; the sensor configured to generate signals based upon such movement, pressure and/or force in an activity approximating sexual sensations, the microprocessor configured for receiving signals from the sensor, the microprocessor adapted to generate a signal intended to represent a sensation in an activity approximating sexual sensations; and the stimulation material covering at least a portion of the surface of the inner cavity for receiving the signal representing a sensation on a penis;
   inserting the unitary prosthetic body in a cavity; and
   simulating sexual sensation by activating said stimulation material with said signal.

* * * * *